United States Patent
Han et al.

(10) Patent No.: US 10,367,145 B2
(45) Date of Patent: Jul. 30, 2019

(54) SELF-ASSEMBLY OF NANOSTRUCTURES

(71) Applicant: INTERNATIONAL BUSINESS MACHINES CORPORATION, Armonk, NY (US)

(72) Inventors: Shu-Jen Han, Cortlandt Manor, NY (US); Bharat Kumar, Tarrytown, NY (US); George S. Tulevski, Croton-on-Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/488,751

(22) Filed: Apr. 17, 2017

(65) Prior Publication Data
US 2018/0111833 A1 Apr. 26, 2018

Related U.S. Application Data

(62) Division of application No. 15/298,620, filed on Oct. 20, 2016, now Pat. No. 9,691,987.

(51) Int. Cl.
| | |
|---|---|
| *H01L 51/00* | (2006.01) |
| *C07F 9/38* | (2006.01) |
| *H01L 21/02* | (2006.01) |
| *C01B 32/174* | (2017.01) |
| *C01B 32/16* | (2017.01) |
| *C01B 32/168* | (2017.01) |

(52) U.S. Cl.
CPC .......... *H01L 51/0048* (2013.01); *C01B 32/16* (2017.08); *C01B 32/168* (2017.08); *C01B 32/174* (2017.08); *C07F 9/3808* (2013.01); *H01L 21/02606* (2013.01); *H01L 51/0012* (2013.01)

(58) Field of Classification Search
USPC ........ 428/221, 332, 357, 364, 402; 988/742, 988/750, 752, 762, 773
See application file for complete search history.

(56) References Cited

U.S. PATENT DOCUMENTS

| | | | | |
|---|---|---|---|---|
| 2006/0099135 | A1* | 5/2006 | Yodh .................. | B82Y 10/00 423/447.1 |
| 2006/0165896 | A1* | 7/2006 | Afzali-Ardakani .... | B05D 1/283 427/258 |
| 2014/0363643 | A1* | 12/2014 | Afzali-Ardakani .... | C08G 75/06 428/210 |

OTHER PUBLICATIONS

Han, et. al., Pending U.S. Appl. No. 15/298,620 entitled "Self-Assembly of Nanostructures," filed Oct. 20, 2016.

(Continued)

*Primary Examiner* — Matthew D Matzek
(74) *Attorney, Agent, or Firm* — Cantor Colburn LLP; Vazken Alexanian

(57) ABSTRACT

Structures and methods that include selective electrostatic placement based on a dipole-to-dipole interaction of electron-rich carbon nanotubes onto an electron-deficient pre-patterned surface. The structure includes a substrate with a first surface having a first isoelectric point and at least one additional surface having a second isoelectric point. A self-assembled monolayer is selectively formed on the first surface and includes an electron deficient compound including a deprotonated pendant hydroxamic acid or a pendant phosphonic acid group or a pendant catechol group bound to the first surface. An organic solvent can be used to deposit the electron rich carbon nanotubes on the self-assembled monolayer.

13 Claims, 2 Drawing Sheets

(56) References Cited

OTHER PUBLICATIONS

Han, et. al., Pending U.S. Appl. No. 15/488,746 entitled "Self-Assembly of Nanostructures," filed Apr. 17, 2017.
Han, et. al., Pending U.S. Appl. No. 15/488,762 entitled "Self-Assembly of Nanostructures," filed Apr. 17, 2017.
List of IBM Patents or Patent Applications Treated as Related; (Appendix P), Date Filed Apr. 24, 2017; 2 pages.

* cited by examiner

SELF-ASSEMBLY OF NANOSTRUCTURES

DOMESTIC PRIORITY

This Application is a DIVISIONAL of U.S. patent application Ser. No. 15/298,620, filed Oct. 20, 2016, the disclosure of which is incorporated by reference herein in its entirety.

BACKGROUND

The present invention relates to structures and methods of placing carbon nanotubes (CNTs) on a substrate. More particularly, the present invention is generally directed to structures and methods that include selective electrostatic placement based on a dipole-to-dipole interaction of electron-rich carbon nanotubes onto an electron-deficient pre-patterned surface.

CNTs can be semiconducting and therefore are of interest for electronic applications. Semiconducting CNTs can replace or complement traditional semiconductors in both high-performance and low-cost thin film transistor devices. To make any electronic device, one needs to precisely place the nanostructure over large areas. Various approaches have been developed for placing CNTs on a substrate.

SUMMARY

In one or more embodiments, a method of forming a structure having selectively placed carbon nanotubes includes providing a substrate including a pattern formed of a first material. The substrate is coated with a solution containing an electron deficient compound including a pendant hydroxamic acid group or a pendant phosphonic acid group or a pendant catechol group, wherein the pendant hydroxamic acid group or the pendant phosphonic acid group or the pendant catechol group is reactive with the pattern formed of the first material to form a bound self-assembled monolayer of the electron deficient compound corresponding to the pattern. The substrate is coated with a solution including carbon nanotubes coated with an electron rich arene, wherein the carbon nanotubes coated with the electron rich arene form a dipole-to-dipole interaction with the electron deficient compound.

In one or more embodiments, a structure having a carbon nanotube (CNT) layer includes a substrate including a first surface having a first isoelectric point and at least one additional surface having a second isoelectric point. A self-assembled monolayer is on the first surface and includes an electron deficient compound including a deprotonated pendant hydroxamic acid or a pendant phosphonic acid group or a pendant catechol group bound to the first surface. Electron rich coated CNTs are on the self-assembled monolayer.

In one or more embodiments, a precursor for making a self-assembled monolayer includes an electron deficient compound including a first functional group selective to anchor the monolayer to a surface, wherein the first functional group includes a phosphonic acid or a hydroxamic acid or a catechol, wherein the surface has an isoelectric point greater than a pKa of the phosphonic acid or the hydroxamic acid or the catechol.

BRIEF DESCRIPTION OF THE DRAWINGS

The following detailed description, given by way of example and not intended to limit the description solely thereto, will best be appreciated in conjunction with the accompanying drawings, wherein like reference numerals denote like elements and parts, in which.

DETAILED DESCRIPTION OF THE DRAWINGS

Figure 1:
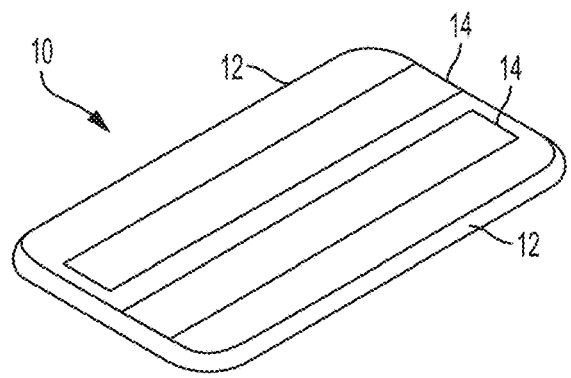
FIG. 1 depicts a perspective view of a lithographically patterned substrate including two different surfaces, each surface having a different isoelectric point in accordance with one or more embodiments of the invention.

The following definitions and abbreviations are to be used for the interpretation of the claims and the specification. As used herein, the terms "comprises," "comprising", "includes", "including", "has", "having", "contains" or "containing", or any other variation thereof, are intended to cover a non-exclusive inclusion. For example, an article or apparatus that comprises a list of elements is not necessarily limited to only those elements but can include other elements not expressly listed or inherent to such article or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

Detailed embodiments of the structures of the present invention are described herein. However, it is to be understood that the embodiments described herein are merely illustrative of the structures that can be embodied in various forms. In addition, each of the examples given in connection with the various embodiments of the invention is intended to be illustrative, and not restrictive. Further, the figures are not necessarily to scale, some features can be exaggerated to show details of particular components. Therefore, specific structural and functional details described herein are not to be interpreted as limiting, but merely as a representative basis for teaching one skilled in the art to variously employ the methods and structures of the present description. For the purposes of the description hereinafter, the terms "upper", "lower", "top", "bottom", "left," and "right," and derivatives thereof shall relate to the described structures, as they are oriented in the drawing figures. The same numbers in the various figures can refer to the same structural component or part thereof.

One approach to placing CNTs on a substrate involves directed assembly of CNTs from a suspension. In this approach, a substrate is patterned to define areas to which the CNT will have an affinity. The affinity is due to functionalization of either the substrate or the CNT to promote covalent or ionic bonding between the substrate and the CNT.

In another approach to place CNTs on a substrate, the prior art stamps a substrate with an organic compound to create a substrate having hydrophilic and hydrophobic regions. The hydrophilic region is the original substrate surface and the hydrophobic region is the area stamped with the organic compound. The substrate is immersed in a solution of CNTs and dried to leave CNTs on the hydrophilic regions. However, the CNTs on the surface of the substrate are bundled (i.e. a group of CNTs twisted together in a rope-like fashion) and/or multilayered. Bundled or multilayered CNTs are undesirable because a transistor made from them requires higher voltage to turn the transistor on and off. The described method has another drawback in that a solution of CNTs is not able to reach recessed hydrophilic areas having small widths (around or less than 200 nm). As a result, CNTs will be placed in large hydrophilic areas while small hydrophilic features remain uncovered. Accordingly, a CNT placement method based upon hydrogen bonding can result in poor selectivity.

Additionally, previous work on self-assembly of nanostructures utilizes external forces such as an electric field or electrostatic forces where the nanostructures were dissolved in water. These types of methods are incompatible with organic solvents.

Described herein are structures and methods for selective electrostatic placement based on a dipole-to-dipole interaction of electron-rich carbon nanotubes and an electron-deficient pre-patterned surface. When the electron-rich carbon nanotubes are deposited onto an electron-deficient pre-patterned surface, the electron rich CNTs self-align to the electron-deficient pre-patterned surface because of the polarity differences, wherein the electron rich CNTs are attracted to and selectively interact with the electron deficient pre-patterned surface. Advantageously, the method and resulting structure can be used to selectively place the CNTs into very narrow trenches of less than 100 nanometers wide and can be applied to other nanoparticles as well.

The electron deficient pre-patterned surface can generally be formed by creating two types of surfaces with different isoelectric points using standard lithography and etching processes followed by selectively functionalizing an electron deficient compound on one of the surfaces. As used herein, the term "isoelectric point" generally refers to the pH at which a particular molecule carries no net electrical charge. In the present invention, the selected surface having a higher isoelectric point than the other surface is used to form the electron deficient pre-patterned surface. Typically, the isoelectric point differential between the surface utilized to form the electron deficient pre-patterned surface and the other surface is at least 3 in one or more embodiments, at least 4 in other embodiments and at least 5 in still other embodiment. By way of example, hafnium oxide having an isoelectric point of about 7 can be used to form the electron deficient pre-patterned surface whereas silicon dioxide having an isoelectric point of about 2 can be used for the other surface, which results in an isoelectric point differential of about 5.

Suitable materials defining the surface for forming the electron deficient pre-patterned surface include, but are not limited to, a metal oxide or a metal nitride whereas the other surface (i.e., the non-electron deficient surface) can be formed of a non-metal oxide, e.g., a silicon oxide ($Si_xO_zH_z$) or a metal such as, but not limited to, gold, palladium, copper, platinum, and the like. The metal oxide includes at least one metal from group IVB, VB, VIB, VIIB, VIII or IIA (CAS version) of the Periodic Table of the Elements. Illustratively, the metal oxide can be an aluminum oxide ($Al_2O_3$), a hafnium oxide ($HfO_2$), a titanium oxide ($TiO_x$), or a zinc oxide (ZnO). Exemplary metal nitrides include silicon nitride and titanium nitride.

It is believed that surfaces with an isoelectric point greater than the pKa of the acid (e.g., hydroxamic, phosphonic, catechol) used for the self-assembly will provide directed self-assembly due to deprotonation of the acid. This is true for silicon nitride, titanium nitride aluminum oxide, hafnium oxide, and the like. Conversely, surfaces with an isoelectric point less than the pKa of the acid (hydroxamic, phosphonic, catechol) used for the self-assembly will give worse/no directed self-assembly. This is true for silicon dioxide.

By carefully selecting the isoelectric charge of one surface relative to another, a selected one of the surfaces can be made to selectively bind the electron deficient compound to the surface. For example, hydroxamic acids and phosphonic acids are known to selectively bind to surfaces that are relatively basic but do not bind to surfaces which are more acidic. Self-assembly will be provided due to deprotonation of the acid because the isoelectric point of the surface can be formed of a material that can be selected to be greater than the pKa of the acid. It is believed catechol will bind in a similar manner via deprotonation of the phenolic hydrogen. Conversely, surfaces with an isoelectric point less than the pKa of the acid used for the self-assembly will give worse/no directed self-assembly. This is true for silicon dioxide. See, for example, J. P. Folkers et al., "Self-assembled monolayers of long-chain hydroxamic acids on the native oxides of metals," *Langmuir,* 11, 813-824 (March 1995), and H. Park et al., "High-density integration of carbon nanotubes via chemical self-assembly," Nature Nanotech., 7, 787-791 (October 2012). The entire contents of each of the foregoing references are incorporated by reference herein. See also, U.S. Patent Application Publication Number 2013/0082233, which describes an exemplary process for decorating a surface of a substrate with a charge. In one exemplary embodiment, the monolayer includes a positively charged pyridinium salt bearing a hydroxamic acid moiety, NMPI (4-(N-hydroxycarboxamido)-1-methylpyridinium iodide).

In view of the foregoing, the electron deficient pre-patterned surface can be formed by selectively reacting an electron deficient compound including a terminal hydroxamic acid or phosphonic acid or catechol functionality with a surface having an isoelectric point greater than the pKa of the particular terminal acid group. Exemplary electron deficient compounds are of formula (I) shown below.

(I)

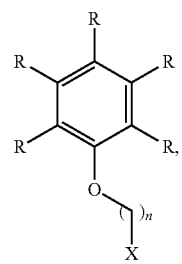

wherein R is an electron withdrawing group, n is an integer from 1 to 12, and X is hydroxamic acid, phosphonic acid or a catechol group. Exemplary electron withdrawing groups include, without limitation, fluorine groups, nitro groups, cyano groups combinations thereof, or the like. The electron deficient compound including the terminal hydroxamic acid or phosphonic acid or catechol functionality can be solvent coated onto the substrate. Exemplary compounds include pentafluorophenoxyhydroxamic acid or pentafluorophenoxyphosphonic acid, wherein the acid moiety selectively binds the electron deficient compound to the patterned metal oxides present on the substrate surface.

Thus, in general, according to the present techniques, those surfaces for which self-assembly of the monolayer is desired will be formed from a material having an isoelectric point greater than the pKa of the acid (hydroxamic, phosphonic, catechol) used for the self-assembly, and those surfaces for which self-assembly of the monolayer is not desired will be formed from a material having an isoelectric point that is less than the pKa of the acid. Non-limiting examples include hafnium oxide and silicon dioxide, respectively.

The nanostructures can be CNTs coated with electron rich arenes, which render the CNTs soluble in organic solvent. The CNTs of the present invention can be formed by any one of several processes including, for example, arc discharge, laser ablation, high pressure carbon monoxide (HiPCO), and chemical vapor deposition (CVD) (e.g., plasma enhanced CVD).

For example, using CVD, a metal catalyst layer of metal catalyst (e.g., including nickel, cobalt, iron, or a combination thereof), is formed on a substrate (e.g., silicon). The metal nanoparticles can be mixed with a catalyst support (e.g., MgO, $Al_2O_3$, etc) to increase the specific surface area for higher yield of the catalytic reaction of the carbon feedstock with the metal particles. The diameters of the nanotubes that are to be grown can be controlled by controlling the size of the metal particles, such as by patterned (or masked) deposition of the metal, annealing, or by plasma etching of a metal layer.

The substrate including the metal catalyst layer can be heated to approximately 700° C. The growth of the CNTs can then be initiated at the site of the metal catalyst by introducing at least two gases into the reactor: a process gas (e.g., ammonia, nitrogen, hydrogen or a mixture of these) and a carbon-containing gas (e.g., acetylene, ethylene, ethanol, methane or a mixture of these)

A plasma can be also be used to enhance the growth process (plasma enhanced chemical vapor deposition), in which case the nanotube growth can follow the direction of the plasma's electric field. By properly adjusting the geometry of the reactor it is possible to synthesize aligned carbon nanotubes.

Generally, the CNTs of the present invention can be electrically and thermally conductive, and have an essentially uniform diameter that is in a range from 1 micron (μm) to 3 μm and a length that is in a range from 1 μm to 10 μm. The CNTs can also be single-walled nanotubes (SWNTs) or multi-walled nanotubes (MWNTs) (e.g., double-walled nanotubes (DWNTs)). The CNTs can also have a zigzag, an armchair, or a chiral arrangement, so long as the resulting CNT-pentacene composite should exhibit good charge carrier mobility (e.g., in the range of 1 $cm^2/V·sec$ to 1000 $cm^2/V·sec$).

The CNTs can also be purified (e.g., by washing in a sodium hypochlorite solution) to remove any contaminants.

The CNTs are then coated with electron rich arenes and dried. As used herein, the term "arene" means an aromatic hydrocarbon, which can contain a single ring or multiple rings or fused rings. In one or more embodiments, the arene is selected from the group consisting of optionally substituted benzene, biphenylene, triphenylene, pyrene, naphthalene, anthracene and phenanthrene or mixtures thereof.

When the electron rich CNTs are coated onto the electron deficient pre-patterned surface, a dipole-dipole interaction occurs to provide selective placement of the CNTs on the substrate. Advantageously, the electron rich CNTS can be deposited in an organic solvent such as by drop casting, spin coating, or immersion coating.

After selectively placing the electron rich CNTs on electron deficient pre-patterned surface, the arenes can be removed from the CNT such as by annealing the device 100.

Figure 2:
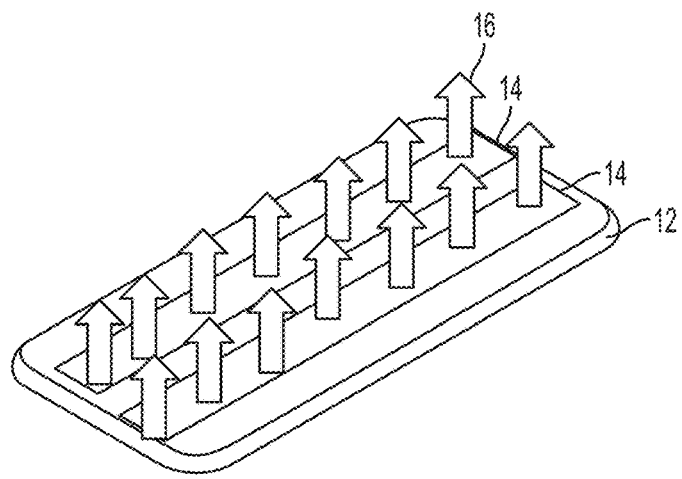
FIG. 2 depicts a perspective view of the lithographically patterned substrate of FIG. 1 subsequent to formation of a self-assembled monolayer of an electron deficient compound so as to form an electron deficient surface on a selected one of the two different surfaces.
Figure 3:
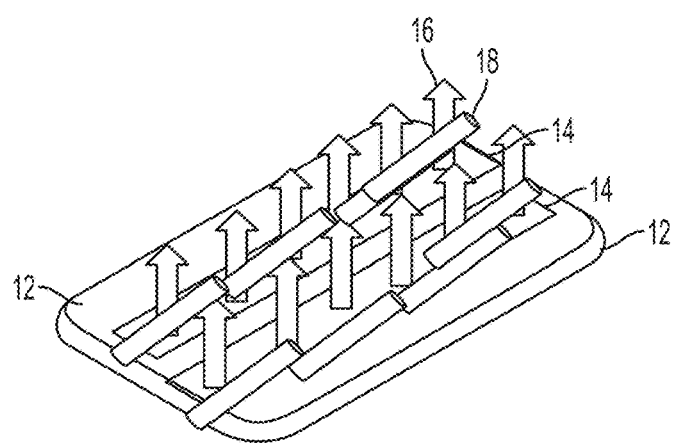
FIG. 3 depicts a perspective view of the substrate of FIG. 2 including the self-assembled monolayer subsequent to selective electrostatic placement of electron-rich carbon nanotubes on the self-assembled monolayer based on a dipole-to-dipole interaction with the electron-deficient surface.

Referring now to FIGS. 1-3, a method of selectively placing the CNTs onto a substrate according to one or more embodiments of this invention is given. In FIG. 1, a substrate 10 is first patterned.

The patterning process generally includes forming two types of surfaces 12, 14 with different isoelectric points as previously discussed using standard lithography and etching processes. The lithographic step can include forming a photoresist (organic, inorganic or hybrid) atop a substrate. In one or more embodiments, the photoresist can be formed directly on the upper surface of the substrate. The photoresist can be formed utilizing a deposition process such as, for example, CVD, PECVD and spin-on coating. Following formation of the photoresist, the photoresist is exposed to a desired pattern of radiation. Next, the exposed photoresist is developed utilizing a conventional resist development process.

After the development step, an etching step can be performed to transfer the pattern from the patterned photoresist into at least the substrate. In one or more embodiments, the pattern can be first transferred into a hard mask material and then into the substrate. In such an embodiment, the patterned photoresist is typically, but not necessarily always, removed from the surface of the structure after transferring the pattern into the hard mask material utilizing a resist stripping process such as, for example, ashing. The etching step used in forming the at least one opening can include a dry etching process (including, for example, reactive ion etching, ion beam etching, plasma etching or laser ablation), a wet chemical etching process or any combination thereof. In one or more embodiments, reactive ion etching is used to form the at least one opening. By way of non-limiting example, the at least one opening can be a trench feature, via feature, combinations thereof, or the like.

Each opening that is formed in the substrate is then filled with material 14 having an isoelectric point different from the material 12 as decried above defining the substrate or a patterned layer thereon. Alternatively, the substrate or the patterned material can be formed of material 14 and each opening filled with material 12. By way of example, the substrate can include a layer of a silicon dioxide layer formed thereon and subjected to the patterning process, wherein the patterned features are subsequently filled with hafnium oxide. As noted above, material 14 is selected to have an isoelectric point that is greater than the pKa of the terminal acid group for the electron deficient compound, thereby resulting in deprotonation of the acid upon contact therewith. In contrast, material 12 is selected to have an isoelectric point that is less than the pKa of the terminal acid group of the electron deficient compound such that deprotonation does not occur.

In FIG. 2, the patterned substrate is put in contact with a solution containing the electron deficient compound including a terminal hydroxamic acid or a terminal phosphonic acid group or catechol group as described above. The terminal hydroxamic acid or the phosphonic acid or the catechol groups (i.e., the phenolic hydrogen) reacts with a selected surface, e.g., material 14, and serves to anchor the electron deficient compound to material 14 of the substrate as indicated by arrows 16. More particularly, the hydroxamic acid or the phosphonic acid or the catechol selectively binds to material 14 present on the substrate so as to form a self-assembled monolayer on the material 14.

In FIG. 3, the substrate with the self-assembled monolayer is put in contact with a solution containing CNTs, wherein the CNTs are coated with an electron rich arene. In one or more embodiments, the solution can be an organic solvent such as but not limited to aliphatics, aromatics, and mixtures thereof such as, for example, toluene, chloroform, hexane, heptane and the like. The electron rich CNTs are electrostatically attracted to the electron deficient self-assembled monolayer based on a dipole-to-dipole interaction.

The substrate is then rinsed in a non-polar solvent to leave a CNT layer 18 above the self-assembled monolayer 16. The rinsing step removes any excess CNTs to form a monolayer of CNT.

Figure 4:
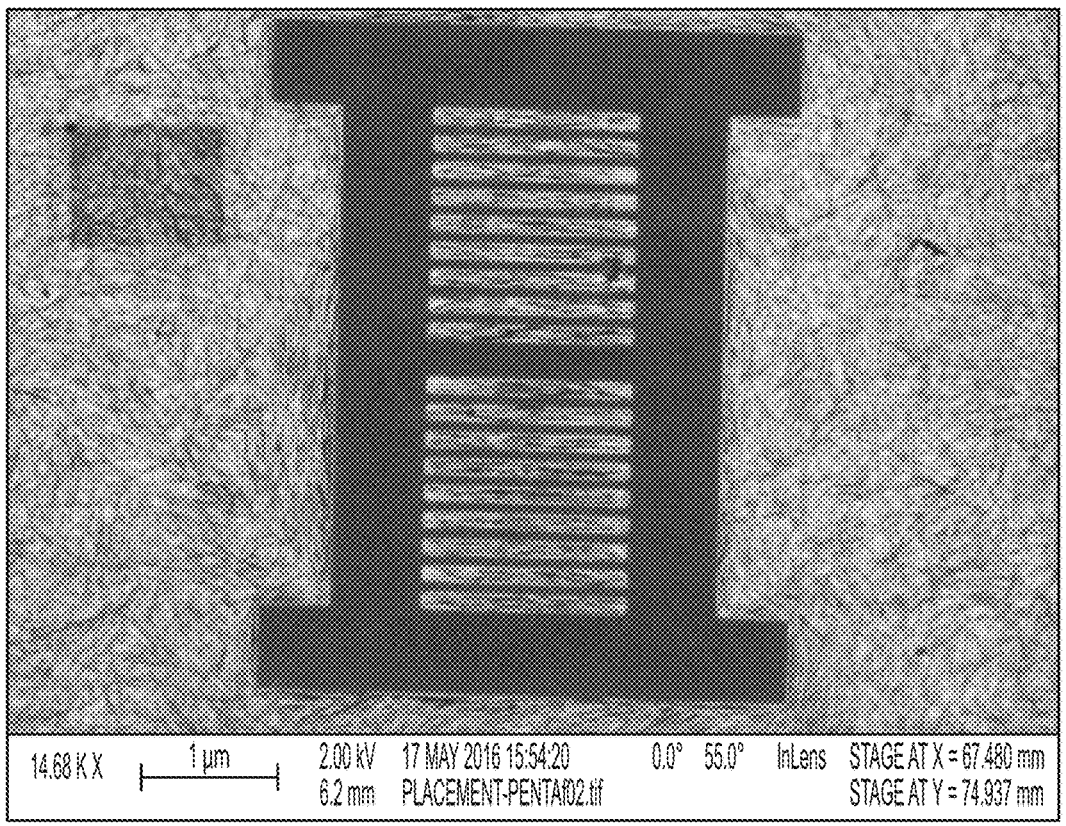
FIG. 4 depicts a scanning electron micrograph of an electronic structure including selectively placed carbon nanotubes in accordance with one or more embodiments of the invention.

FIG. 4 is a scanning electron micrograph demonstrating selective placement of CNTs onto a substrate in accordance with the present invention. The substrate included a surface formed of silicon dioxide that was lithographically patterned and etched to form a repeating 150 nm trench feature. The trench features were filled with hafnium oxide and coated with pentafluorophenoxyhydroxamic acid to form an electron deficient self-assembled monolayer on the hafnium oxide. A solution of arene coated CNTs was applied to the substrate and subsequently rinsed. The excess CNTs were removed by the rinsing to provide a selectively placed layer of CNTs on the electron deficient self-assembled monolayer pattern but did not form over the silicon dioxide.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A structure having layer of carbon nanotubes (CNTs), the structure comprising:
   a substrate including a first surface having a first isoelectric point and at least one additional surface having a second isoelectric point;
   a self-assembled monolayer on the first surface, the self-assembled monolayer comprising an electron deficient compound of the formula:

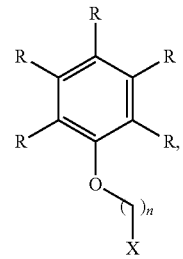

wherein R is an electron withdrawing group, n is an integer from 1 to 12, and X is hydroxamic acid or phosphonic acid or catechol that is bound to the first surface; and
   electron rich coated CNTs on the self-assembled monolayer, wherein the electron rich coated CNTs form a dipole-to-dipole interaction with the electron deficient compound, wherein the electron rich coated CNTs comprise a coating of an arene on the CNT, wherein the arene is selected from the group consisting of benzene, biphenylene, triphenylene, pyrene, naphthalene, anthracene and phenanthrene and mixtures thereof.

2. The substrate of claim 1, wherein the first surface is a metal oxide and the at least one additional surface is a non-metal oxide.

3. The structure of claim 1, wherein the first isoelectric point is greater than the second isoelectric point and is at a differential of at least 3.

4. The structure of claim 1, wherein the electron withdrawing group comprises a fluorine group, a nitro group, a cyano group or mixtures thereof.

5. The structure of claim 1, wherein the electron deficient compound is pentafluorophenoxyhydroxamic acid, pentafluorophenoxyphosphonic acid or mixtures thereof.

6. The structure of claim 1, wherein the first surface comprises a metal oxide or metal nitride.

7. The structure of claim 6, wherein the metal oxide includes at least one metal from group IVB, VB, VIB, VIIB, VIII or IIA (CAS version) of the Periodic Table of the Elements.

8. The structure of claim 1, wherein the first isoelectric point is greater than a pKa of the electron deficient compound and the second isoelectric point is less than the pKa of the electron deficient compound.

9. The structure of claim 1, wherein the first isoelectric point is greater than the second isoelectric point and is at a differential of at least four.

10. The structure of claim 1, wherein the first surface comprises a hafnium oxide surface and the at least one additional surface comprises silicon dioxide.

11. The structure of claim 1, wherein the carbon nanotubes have a length that is in a range from 1 μm to 10 μm.

12. The structure of claim 6, wherein the metal oxide comprises aluminum oxide ($Al_2O_3$), a hafnium oxide ($HfO_2$), a titanium oxide ($TiO_x$), or a zinc oxide (ZnO).

13. The structure of claim 6, wherein the metal nitride comprises titanium nitride or silicon nitride.

* * * * *